United States Patent [19]

Ogawa et al.

[11] 4,063,894
[45] Dec. 20, 1977

[54] TEST STRIP FOR THE DETECTION OF OCCULT BLOOD IN EXCRETA

[75] Inventors: Yasunao Ogawa, Ikeda; Yukio Yonetani, Nara, both of Japan

[73] Assignee: Shionogi & Co., Ltd., Osaka, Japan

[21] Appl. No.: 733,913

[22] Filed: Oct. 19, 1976

[30] Foreign Application Priority Data

Nov. 21, 1975 Japan .................................. 50-140428

[51] Int. Cl.² ........................ C09K 3/00; G01N 31/22; G01N 33/16
[52] U.S. Cl. .............................. 23/230 B; 23/253 TP; 252/408
[58] Field of Search ........................ 23/230 B, 253 TP; 195/103.5 R; 252/408

[56] References Cited

U.S. PATENT DOCUMENTS

| | | | |
|---|---|---|---|
| 3,252,762 | 5/1966 | Adams, Jr. et al. | 23/230 B UX |
| 3,853,471 | 12/1974 | Rittersdorf et al. | 23/230 B |
| 3,975,161 | 8/1976 | Swoboda et al. | 23/253 TP |
| 3,986,833 | 10/1976 | Mast et al. | 23/230 B |
| 4,017,261 | 4/1977 | Swoboda et al. | 23/253 TP |

*Primary Examiner*—Joseph Scovronek
*Attorney, Agent, or Firm*—Birch, Stewart, Kolasch and Birch

[57] ABSTRACT

A test strip for detecting the presence of occult blood in excreta such as urine or feces or body fluid, which strip comprises a bibulous or porous material impregnated with a chromogen, a hydroperoxide and, as a sensitizer, a thiazole compound of the formula:

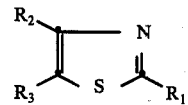

wherein $R_1$ is a lower alkyl; a substituted or unsubstituted aralkenyl, or a substituted or unsubstituted aralkyl; $R_2$ and $R_3$ are each a hydrogen or a lower alkyl; and $R_2$ and $R_3$, when taken together with the adjacent carbon atoms, may form a benzene ring.

18 Claims, No Drawings

TEST STRIP FOR THE DETECTION OF OCCULT BLOOD IN EXCRETA

BACKGROUND OF THE INVENTION

1. Field of the Invention

This invention relates to a test strip for occult blood detection in excreta, comprising a chromogen, a hydroperoxide and, as a sensitizer, a thiazole compound. More particularly, the present invention is concerned with a test strip for occult blood detection in excreta such as urine or feces, comprising a chromogen, a hydroperoxide and, as a sensitizer, thiazole compound (I) of the formula:

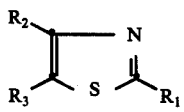

wherein $R_1$ is an alkyl, a substituted or unsubstituted aralkenyl, or a substituted or unsubstituted aralkyl; $R_2$ and $R_3$ are each a hydrogen or an alkyl; and $R_2$ and $R_3$, when taken together with the adjacent carbon atoms, may form a benzene ring.

The test strip in accordance with the present invention can be used for the detection of occult blood in excreta (e.g. urine, feces), vomit, substances in the stomach, or spinal fluid. It is recognized that such hemorrhage is caused by cancer, ulcer, piles, typhus, scorbutus, purpura, renal insufficiency, bladder stones, kidney stones, and the like. Hemoglobin resulting from such diseases is usually in a very small quantity, and therefore cannot be examined with the eye unaided or through a microscope. According to the test strip of the invention, the occult blood can be easily and reliably detected with high sensitivity. Thus, the test strip of the invention is useful in early diagnosis of the diseases mentioned above.

2. Description of the Prior Art

The principle for the detection of occult blood is well known, i.e. hemoglobin in the blood catalyzes to decompose a hydroperoxide, and the liberated oxygen is transferred to a chromogen which is oxidized to give a colored substance, indicating the presence of occult blood. However, a test strip which is prepared by direct application of this principle does not give a satisfactory result in the detection of a very small amount of blood. Also, the test strip so prepared has a drawback in its insufficient stability during storage.

As a test strip including a sensitizer in addition to a chromogen for occult blood detection, there has hithertofore been known a test strip using quinine (Japanese Pat. No. 478,815) and a test strip using a phenanthridine (U.S. Pat. No. 3,853,472). However, the former does not have a sufficient sensitivity and the latter has a drawback that it contains a carcinogenic substance as a sensitizer. The sufficient sensitivity of the rapid test for occult blood is of decisive importance, and the safety in its handling must be considered. It is recognized in the art that in view of practical clinical application, sensitivity to detect blood with a concentration of more than 1:200,000 in dilution is required. Also, the physicians concerned have pointed out that excessive sensitivity in such test strip is not desirable, because a false positive color reaction may take place.

Apart from this prior art, a use of pyridine derivatives has recently been proposed in, for instance, U.S. Pat. No. 3,917,452. Although this proposal asserts that it can detect blood in the dilution of 1:1,000,000, it has not been commercially exploited and an accurate assessment of the actual advantages in enhancement of the sensitivity of diagnosis has therefore not been made yet.

SUMMARY OF THE INVENTION

The present inventors who had long been studying for enhancement of the sensitivity of the test strip for occult blood, have now discovered that a thiazole compound (I) as mentioned above has a suitable activating property for occult blood detection. The present invention has been completed on the basis of these discoveries.

Accordingly, it is a primary object of the present invention to provide a test strip for detecting the presence of occult blood readily and reliably.

Another object of the present invention is to provide a simple, rapid and convenient method for detecting occult blood in excreta or body fluids, particularly in urine.

According to the present invention, there is provided a test strip for occult blood detection, which contains, as a sensitizer, a thiazole compound (I) of the formula:

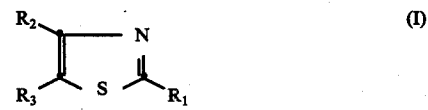

wherein $R_1$ is an alkyl, a substituted or unsubstituted aralkenyl, or a substituted or unsubstituted aralkyl; $R_2$ and $R_3$ are each a hydrogen or an alkyl; and $R_2$ and $R_3$, when taken together with the adjacent carbon atoms, may form a benzene ring.

In the thiazole compound (I), the alkyl group for $R_1$, $R_2$ and $R_3$ is preferably a $C_{1\sim3}$ alkyl (e.g. methyl, ethyl or propyl). Also, preferred substituents for $R_1$ can be a substituted or unsubstituted aralkenyl (II) and a substituted or unsubstituted aralkyl (III), as shown in the following formulae:

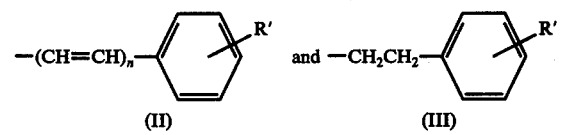

wherein $n$ is an integer of 1 or 2; $R'$ is hydrogen, halogen (e.g. iodine, chlorine, bromine, fluorine), a $C_{1\sim3}$ alkyl (e.g. methyl, ethyl, propyl), or a $C_{1\sim3}$ alkoxy (e.g. methoxy, ethoxy, propoxy).

Typical examples of the thiazole compound coming within the scope of general formula (I) are 2-styryl-4-methylthiazole, 2-(p-methoxystyryl)-thiazole, 2-(p-ethoxystyryl)-thiazole, 2-(p-methoxystyryl)-4-methyl-thiazole, 2-styrylthiazole, 1-phenyl-4-thiazolyl-(2)-butadiene, 2-(p-methylstyryl)-thiazole, 2-(p-methoxystyryl)-benzothiazole, 2-(styryl)-benzothiazole, 2-(p-chlorostyryl)-thiazole, 2-(p-bromostyryl)-thiazole, 2-(p-fluorostyryl)-thiazole, 2,4-dimethyl-thiazole, 1-phenyl-2-(2-thiazole)ethane and the like.

It is, of course, obvious that not all of the compounds coming within the scope of general formula (I) possess sensitizing properties of the same degree. Thus, it is possible to adjust the sensitivity of, for example, a blood test in accordance with practical requirements. For example, test strips of increasing activity are obtained, when, as a sensitizer, there are used the compounds set forth in the following and in the given order: 2-styryl-4-methylthiazole, 2-(p-methoxystyryl)-thiazole, 2-(p-methoxystyryl)-4-methylthiazole > 2-styrylthiazole, 2-(p-methoxystyryl)-thiazole, 1-phenyl-4-thiazolyl-(2)-butadiene, 2-(p-methoxystyryl)-benzothiazole > 2,4-dimethylthiazole, 1-phenyl-2-(2-thiazole)-ethane, 2-(p-chlorostyryl)-thiazole, (2-styryl)-benzothiazole.

The test strip of the invention may be prepared by, for instance impregnating an absorbing material with all of the reagents necessary for the color reaction. This impregnating process may preferably comprise two steps. First, an absorbing material is impregnated with an emulsion containing hydroperoxide, emulsifier, adhesive agent, buffer, pigment, and stabilizer for hydroperoxide. Then, the impregnated material is dried and impregnated with a solution of sensitizer (I) and chromogen.

The thus obtained absorbing material is dried to give a desired test strip. Although the above-mentioned method is a preferred one, the order in the impregnating process is not necessarily critical and may include many variations.

The sensitizer (I) can be any substance of those as mentioned above, and it is preferably used in an amount of about 0.5-10 times by weight of a chromogen used.

Examples of the absorbing material can be filter paper, ion-exchange cellulose paper, fiber and material having equivalent absorbing properties.

Hydroperoxides include, for example, cumene hydroperoxide, p-menthane hydroperoxide, tetraline hydroperoxide, tert-butyl hydroperoxide, 2,5-dimethylhexane-2,5-dihydroperoxide and diisopropyl-benzene hydroperoxide. Other hydroperoxides which liberate oxygen in the presence of blood and catalyzes the oxidation of chromogen, whereby detectable color change takes place, can be similarly used. These hydroperoxides are employed in an amount sufficient to oxidize chromogen in the presence of blood, thereby to produce a colored material, but they are usually used in an excess amount.

As an emulsifier are exemplified gum arabic and polyvinyl alcohol, and they are used usually at a concentration of 12.5-25% (w/v). Also, about 5% (w/v) sodium lauryl sulfate is preferably employed as a stabilizer for the hydroperoxides used.

Gelatin is effective for microencapsulation of the hydroperoxides used. It is preferred to use gelatin at about 10% (w/v) concentration.

Examples of buffer are a citrate, phosphate, phthalate, oxalate, carbonate, and organic or inorganic acid-morpholine (or its derivative, e.g. N-ethylmorpholine). These buffers are used to keep the impregnating solution at pH 5-7, preferably at pH 5-6.

The chromogen may be exemplified as diaminodiphenyl derivatives which include, among others, benzidine, O-tolidine, m-tolidine, dianisidine, 3,3',5,5'-tetramethylbenzidine and salts thereof with a mineral acid (e.g., hydrochloric acid, hydrobromic acid, nitric acid or sulfuric acid). In addition to this, guaiac as its chloroform extracts may also be available. Among these, o-tolidine or N-alkylderivatives thereof are most preferred from a practical point of view.

A pigment such as tartrazine may be added as a background adjusting dye for facilitating the determination of the result of the color development. In preparing the impregnating solution, water, ethanol, chloroform and toluene are used as a solvent.

The test strip of the present invention can detect blood at a concentration of 1:500,000 ~ 1:1,000,000 in dilution. The sensitivity of the test strip containing no sensitizer can detect blood only at a concentration of 1:10,000 ~ 1:30,000 in dilution. Thus, the test strip having a low sensitivity cannot be applied to clinical tests. The test strip of the present invention can detect occult blood in excreta or body fluids, particularly in urine.

The concept of the invention can be applied to a composition as well as to a test strip. The composition can be prepared in a conventional manner as has been adopted in the field of pharmaceutical science. However, in view of their stability and handling, they are preferably employed in the form of a test strip.

The thiazole compound (I) may be prepared by the following equation:

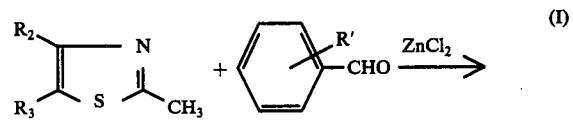

wherein $R_2$, $R_3$ and $R'$ have each the same meaning as defined above. Namely, compound I may be prepared by reacting a corresponding 2-methylthiazole with a corresponding aldehyde under heating in the presence of a Lewis acid (e.g. zinc chloride).

DESCRIPTION OF THE PREFERRED EMBODIMENTS

The working examples are given below to illustrate the embodiments of the present invention, and it is construed that the technical scope of the invention is not limited by the examples given.

EXAMPLE 1

A filter paper (Toyo filter paper No. 131) is impregnated with an emulsion which comprises:

| [First Solution] | |
|---|---|
| 25% (w/v) gum arabic | 10 ml |
| 5% (w/v) sodium lauryl sulfate | 2 ml |
| cumene hydroperoxide | 1 ml |
| 10% (w/v) gelatine-0.2M citrate buffer (pH 5.0) | 5 ml |
| 1% (w/v) tartrazine/aqueous ethanol | 0.5 ml |
| 2M citric acid-N-ethylmorpholine (pH 5.5) | 20 ml |

The paper is taken from the solution and dried at 60°-80° C for 5-10 hours. Then, the paper is impregnated with the second solution which comprises:

| [Second Solution] | |
|---|---|
| o-tolidine | 50 mg |
| 2-styryl-4-methylthiazole | 50 mg |
| chloroform | 10 ml |

The paper is withdrawn and dried for 30 minutes under reduced pressure in a dark place. Then, the paper is cut into a suitable size and stuck onto a polyvinyl chloride sheet for its convenient use. Since there was no difference in the preliminary color reactions using human blood and rat blood, the test color reaction was conducted using rat blood. The blood was submitted to 100-fold dilution with water, and then further with urine of a normal adult. When the test strip of the invention was dipped in samples with various diluted concentrations of blood, the blood of 1:1,000,000 was detectable, through the color reaction was somewhat weak. The determination was made 30 seconds after the impregnation. The test strip (yellow) of the invention turned color to greenish yellow~green~dark blue, depending on the diluted concentration of blood.

The test strip obtained above shows good sensitivity to occult blood, and the test results are shown in the following table wherein Labstix was used for comparison. Labstix is a commercially available test strip for occult blood detection and contains cumene hydroperoxide, o-tolidine and citrate buffer.

Table 1:

| Sensitivity of the test strip for occult blood in urine | | |
|---|---|---|
| Concentration of diluted blood in urine | Labstix | Test strip of the invention |
|  |  | H-L/S* |
| 0 | − | 10Y-9/6 |
| 1/400,000 | ± | 7.5GY-8/6 |
| 1/200,000 | ± | 10GY-8/6 |
| 1/100,000 | + | 5G-6/6 |
| 1/50,000 | ++ | 5BG-5/6 |
| 1/10,000 | ++~+++ | 2.5B-4/6 |

Note:
H-L/S* means hue-lightness/saturation, respectively, and the color reaction is expressed according to Standard Color Chip (JIS (Japanese Industrial Standard) Z 8721-1964). The color reaction with Labstix is expressed in terms of standard color chip accompanied. −: negative reaction, ±: very weak reaction, +, ++, +++: positive color reaction. The color reaction was determined 30 seconds after the impregnation of the test strip with the test sample. Y=yellow, GY=greenish yellow, G=green, BG=blue green, B=blue.

As is apparent from the above table, the test strip of the invention can detect reliably urinary occult blood having a concentration of 1:400,000 in dilution. A diluted blood of 1:1,000,000 is detectable by the test strip of the invention, but the color intensity is somewhat weak. However, detection of blood diluted in 1:400,000 is sufficient for clinical applications.

The sensitivity and stability of test strips containing various sensitizers during their storage under various conditions were examined, and the test results are shown in the following table.

Table 2:

| Sensitivity and stability of test strips with various sensitizers | | | | |
|---|---|---|---|---|
| Sensitizer | Grade of occult blood (detected by Labstix) | Freshly prepared | Stored for a month at 40° C | room temp. |
|  |  | H-L/S (JIS Z 8721-1964) | | |
| 2-(Styryl)-4-methylthiazole | − | 10Y-9/6 | 5Y-9/6 | 5Y-8/5 |
|  | + | 10GY-7/6 | 5GY-8/6 | 5Y-7/7 |
|  | ++ | 5G-7/4 | 2.5G-7/6 | 10Y-8/4 |
| 2-(p-Methoxystyryl)thiazole | − | 7.5Y-9/4 | 5Y-9/6 | 5Y-8/5 |
|  | + | 5GY-9/6 | 10Y-9/6 | 5Y-8/6 |
|  | ++ | 2.5G-7/6 | 7.5GY-8/6 | 2.5GY-8/6 |
| 2-(p-methoxystyryl)-4-methylthiazole** | − | 10Y-9/6 | 5Y-9/6 | 5Y-8/5 |
|  | + | 2.5GY-9/8 | 10Y-9/6 | 5Y-8/6 |
|  | ++ | 5GY-8/8 | 7.5GY-8/6 | 2.5GY-8/6 |

Note:
All the symbols have the same meaning as defined in table 1. *, **: the test strip containing these sensitizers are prepared according to the method as described in Example 2.

From the above table, it is clear that the test strips containing thiazole compounds of the invention show good stability during storage at 4° C for a month. Particularly, the test strip containing 2-(styryl)-4-methylthiazole possesses good stability. However, the stability of the test strips of the invention is somewhat lowered when it is stored at room temperature.

The stability test of the test strips containing various chromogens were carried out, and the test results are shown in the following table.

Table 3:

| Effect of chromogens on the color reaction of test strips after their storage | | | | | |
|---|---|---|---|---|---|
| Preparation | Preservation conditions | Blood concentration in urine | | | |
|  |  | − | + | ++ | +++ |
|  |  | (H-L/S) (JIS Z 8721-1964) | | | |
| I* | Freshly prepared | 10Y-9/6 | 10GY-8/5 | 7.5G-6/5 | 2.5B-4/8 |
|  | 13 days, 4° C | 7.5Y-9/8 | 2.5G-6/6 | 5BG-5/6 | 5B-3/4 |
|  | 13 days, r.t. | 5Y-9/6 | 10GY-7/6 | 10G-5/6 | 5B-3/4 |
|  | 23 days, 4° C | 10Y-9/6 | 7.5G-6/6 | 7.5BG-5/7 | 5B-5/7 |
|  | 23 days, r.t. | 7.5Y-9/6 | 10GY-8/5 | 10G-5/6 | 2.5B-4/8 |
|  | 34 days, 4° C | 10Y-9/6 | 2.5G-7/6 | 2.5BG-5/6 | 5B-4/6 |
|  | 34 days, r.t. | 5Y-8/6 | 10Y-8/6 | 10G-6/6 | 7.5BG-4/6 |
| II** | Freshly prepared | 10Y-9/6 | 7.5GY-8/6 | 2.5G-7/8 | 2.5B-4/6 |
|  | 13 days, 4° C | 10U-9/6 | 7.5GY-8/6 | 7.5G-7/6 | 10BG-4/8 |
|  | 13 days, r.t. | 10Y-9/6 | 5GY-8/6 | 2.5G-7/6 | 7.5BG-4/6 |
|  | 23 days, 4° C | 10Y-9/6 | 7.5GY-8/6 | 2.5BG-5/7 | 7.5BG-5.6 |
|  | 23 days, r.t. | 10Y-9/6 | 10Y-9/6 | 2.5GY-9/6 | 7.5GY-8/5 |
|  | 34 days, 4° C | 10Y-9/6 | 5GY-8/6 | 5G-6/6 | 5BG-5/6 |
|  | 34 days, r.t. | 10Y-9/6 | 10Y-9/6 | 10Y-9/6 | 2.5GY-9/6 |

Note:
*, **: Preparation I contains o-tolidine as a chromogen and Preparation II contains 3,5,3',5'-tetramethylbenzidine. Preparation II is obtained in the same manner as described above.

Occult blood of patients are contained as hemolytic blood or intact non-hemolytic blood, and the ratio of both in urine is not definite. In general, the ratio of hemolytic blood in the urine sample is increased with the lapse of time. Therefore, it was meaningful to examine the color reaction using both urine samples. The test results are shown in the following table.

Table 4:

| Test sample | Time (sec.) | Color reaction of test strip to hemolytic blood and intact blood in urine | | | | |
|---|---|---|---|---|---|---|
| | | Number of erythrocyte in urine sample (Number/μl) | | | | |
| | | 0 | 5 | 10 | 50 | 100 |
| I | 30 | 7.5Y-9/8 | 10Y-8/7 | 2.5GY-8/5 | 5GY-8/6 | 2.5G-6/6 |
| | 60 | 7.5Y-9/8 | 10Y-8/6 | 5GY-8/5 | 7.5GY-8/5 | 7.5G-5/6 |
| II | 30 | 7.5Y-9/8 | 7.5Y-9/8 | 10Y-9/6 | 7.5GY-8/6 | 5G-6/7 |
| | 60 | 7.5Y-9/8 | 10Y-9/6 | 2.5GY-8/6 | 10GY-7/6 | 7.5G-5/7 |
| III | 30 | 5Y-9/6 | 5Y-9/6 | 7.5Y-8/6 | 10Y-9/6 | 2.5G-7/6 |
| | 60 | 5Y-9/6 | 5Y-9/6 | 10Y-8/6 | 2.5GY-8/6 | 7.5G-6/6 |
| IV | 30 | 5Y-9/6 | 5Y-9/6 | 5Y-9/6 | 7.5Y-8/6 | 10Y-8/6 |
| | 60 | 5Y-9/6 | 5Y-9/6 | 5Y-9/6 | 10Y-8/4 | 2.5GY-8/6 |

Note:
I: diluted with distilled water (hemolytic blood)
II: diluted with an isotonic solution (intact blood)
III: diluted in 1:100 with water, and then further diluted with urine (hemolytic blood)
IV: diluted with urine (intact blood). The erythrocyte suspension was prepared from rat blood by washing with an isotonic solution. The color reaction was determined 30 or 60 seconds after the impregnation of the test strip obtained in EXAMPLE 1.

It is seen from the table that the test strip of the invention is more sensitive to hemolytic blood in urine than to non-hemolytic blood.

EXAMPLE 2

2-(P-methoxystyryl)-thiazole, 2-(p-methoxystyryl)-4-methylthiazole, 2-styrylthiazole, 1-phenyl-4-thiazolyl-(2)-butadiene, 2-(p-methylstyryl)-thiazole, 2-(p-methoxystyryl)-benzothiazole, 2-(styryl)-benzothiazole, 2-(p-chlorostyryl)-thiazole, 2,4-dimethylthiazole or 1-phenyl-2-(2-thiazole)ethane is employed as a substitute of 2-styryl-4-methylthiazole of EXAMPLE 1. The procedures similar to those described in EXAMPLE 1 are repeated to give test strips, each of which show the same color reaction with that obtained in EXAMPLE 1.

EXAMPLE 3

Diethylaminoethyl cellulose paper (DE-81, Product of Whatman Co.) is dipped in the following solution (First Solution).

| [First Solution] | |
|---|---|
| 10% (w/v) polyvinyl alcohol 500 | 10 ml |
| 5% (w/v) sodium lauryl sulfate | 4 ml |
| cumene hydroperoxide | 3 ml |
| 10% albumin-0.2M citrate buffer (pH 5.0) | 10 ml |
| 1% (w/v) tartrazine-aqueous ethanol | 0.5 ml |
| 2M Citric acid-morpholine mixture (pH 5.5) | 20 ml |

The impregnated paper is withdrawn, dried at 60°–80° C for 5–10 hours, and impregnated in the second solution below.

| [Second Solution] | |
|---|---|
| o-tolidine | 100 mg |
| 2-(p-methoxystyryl)-thiazole | 50 mg |
| toluene | 10 ml |

The impregnated paper is withdrawn and dried in a dark place for 30 minutes under reduced pressure to give a desired test strip. This test strip shows the same sensitivity to the blood test in urine with that of the test strip in EXAMPLE 1.

By changing citric acid-N-ethylmorpholine to citric acid-morpholine and increasing the amount of o-tolidine to 100 mg in EXAMPLE 1, the same procedure is performed to give a test strip with high sensitivity.

What we claim is:

1. A test strip for detecting occult blood in excreta or body fluids, which strip comprises a porous or bibulous absorbing material impregnated with a chromogen, a hydroperoxide and, as a sensitizer, a thiazole compound (I) of the formula:

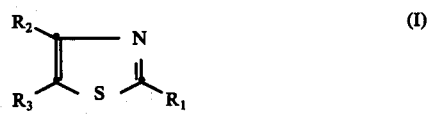

wherein $R_1$ is a lower alkyl, a substituted or unsubstituted aralkenyl, or a substituted or unsubstituted aralkyl; $R_2$ and $R_3$ are each a hydrogen or a lower alkyl; and $R_2$ and $R_3$, when taken together with the adjacent carbon atoms, may form a benzene ring.

2. A test strip for detecting occult blood in excreta according to claim 1, wherein
$R_1$ is a $C_1 \sim C_3$ alkyl, a substituted or unsubstituted aralkenyl of the formula:

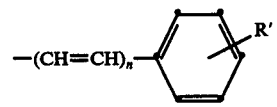

wherein $n$ is an integer of 1-2 and R' is a member selected from the group consisting of a hydrogen, a halogen, a $C_1 \sim C_3$ alkyl and a $C_1 \sim C_3$ alkoxy, or
a substituted or unsubstituted aralkyl of the formula:

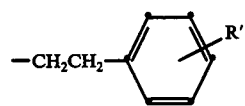

wherein R' has the same meaning as defined above;
$R_2$ and $R_3$ are each a hydrogen or a $C_1 \sim C_3$ alkyl; and
$R_2$ and $R_3$, when taken together with the adjacent carbon atoms, may form a benzene ring.

3. A test strip for occult blood in excreta or body fluids according to claim 1, wherein the thiazole compound (I) is a member selected from the group consisting of 2-styryl-4-methylthiazole, 2-(p-methoxystyryl)-thiazole, 2-(p-ethoxystyryl)-thiazole, 2-(p-methoxystyryl)-4-methylthiazole, 2-styryl-thiazole, 1-phenyl-4- thiazolyl-(2)-butadiene, 2-(p-methylstyryl)-thiazole, 2-(p-methoxystyryl)-benzothiazole, 2-(styryl)-benzothiazole, 2-(p-chlorostyryl)-thiazole, 2-(p-bromostyryl)-thiazole, 2-(p-fluorostyryl)-thiazole, 2,4-dimethylthiazole and 1-phenyl-2-(2-thiazole)-ethane.

4. A test strip for occult blood in excreta or body fluids according to claim 1, wherein the chromogen is a member selected from the group consisting of diaminodiphenyl derivatives benzidine, o-tolidine, m-tolidine, dianisidine and 3,3',5,5'-tetramethylbenzidine, and salts thereof, and guaiac and extracts thereof.

5. A test strip for occult blood in excreta or body fluids according to claim 1, wherein the hydroperoxide is a member selected from the group consisting of cumene hydroperoxide, p-menthane hydroperoxide, tetraline hydroperoxide, tert-butyl hydroperoxide, 2,5-dimethylhexane-2,5-dihydroperoxide and diisopropyl-benzene hydroperoxide.

6. A test strip for occult blood in excreta or body fluids comprising a bibulous or porous absorbing material impregnated with an emulsion which is composed of 25% (w/v) gum arabic, 5% (w/v) sodium lauryl sulfate, cumene hydroperoxide, 10% (w/v) gelatine-0.2M citrate buffer (pH 5.0), 1% (w/v) tartrazine/aqueous ethanol and 2M citric acid-N-ethylmorpholine (pH 5.5) and after drying, with a solution which is composed of o-tolidine, 2-styryl-4-methylthiazole and chloroform.

7. A process for preparing a test strip for occult blood in excreta or body fluids which comprises impregnating a porous or bibulous absorbing material with a solution containing essentially a chromogen, a hydroperoxide and, as a sensitizer, a thiazole compound (I) of the formula:

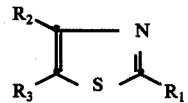

wherein $R_1$ is a lower alkyl, a substituted or unsubstituted aralkenyl, or a substituted or unsubstituted aralkyl; $R_2$ and $R_3$ are each a hydrogen or a lower alkyl; and $R_2$ and $R_3$, when taken together with the adjacent carbon atoms, may form a benzene ring.

8. A process for preparing a test strip for occult blood in excreta or body fluids according to claim 7, wherein
$R_1$ is a $C_1 \sim C_3$ alkyl, a substituted or unsubstituted aralkenyl of the formula:

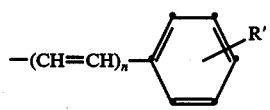

wherein $n$ is an integer of 1–2 and R40 is a member selected from the group consisting of a hydrogen, a halogen, a $C_1 \sim C_3$ alkyl group, and a $C_1 \sim C_3$ alkoxy, or a substituted or unsubstituted aralkyl group of the formula:

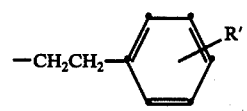

wherein R' has the same meaning as defined above;
$R_2$ and $R_3$ are each a hydrogen or a $C_1 \sim C_3$ alkyl; and
$R_2$ and $R_3$, when taken together with the adjacent carbon atoms, may form a benzene ring.

9. A process for preparing a test strip for occult blood in excreta or body fluids according to claim 7, wherein the thiazole compound (I) is a member selected from the group consisting of 2-styryl-4-methylthiazole, 2-(p-methoxystyryl)-thiazole, 2-(p-ethoxystyryl)-thiazole, 2-(p-methoxystyryl)-4-methylthiazole, 2-styrylthiazole, 1-phenyl-4-thiazolyl-(2)-butadiene, 2-(p-methylstyryl)-thiazole, 2-(p-methoxystyryl)-benzothiazole, 2-(styryl)-benzothiazole, 2-(p-chlorostyryl)-thiazole, 2-(p-bromostyryl)-thiazole, 2-(p-fluorostyryl)-thiazole, 2,4-dimethylthiazole and 1-phenyl-2-(2-thiazole)-ethane.

10. A process for preparing a test strip for occult blood in excreta according to claim 7, wherein the chromogen is a member selected from the group consisting of diaminodiphenyl derivatives benzidine, o-tolidine, m-tolidine, dianisidine, 3,3',5,5'-tetramethylbenzidine, and salts thereof, and guaiac and extracts thereof.

11. A process for preparing a test strip for occult blood in excreta or body fluids, wherein the hydroperoxide is a member selected from the group consisting of cumene hydroperoxide, p-menthane hydroperoxide, tetraline hydroperoxide, tert-butyl hydroperoxide, 2,4-dimethylhexane-2,5-dihydroperoxide and diisopropyl-benzene hydroperoxide.

12. A process for preparing a test strip for occult blood in excreta or body fluids, which comprises impregnating a bibulous or porous absorbing material with an emulsion which is composed of 25% (w/v) gum arabic, 5% (w/v) sodium lauryl sulfate, cumene hydroperoxide, 10% (w/v) gelatine-0.2M citrate buffer (pH 5.0), 1% (w/v) tartrazine/aqueous ethanol and 2M citric acid-N-ethylmorpholine (pH 5.5); drying the impregnated and absorbed material; impregnating the said material with a solution which is composed of o-tolidine, 2-styryl-4-methylthiazole and chloroform; and drying the resultant material to give the desired test strip.

13. A composition for occult blood determination, which comprises a chromogen, a hydroperoxide and, as a sensitizer, a thiazole compound (I) of the formula:

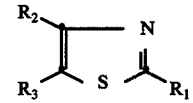

wherein $R_1$ is a lower alkyl, a substituted or unsubstituted aralkenyl, or a substituted or unsubstituted aralkyl; $R_2$ and $R_3$ are each a hydrogen or a lower group; and $R_2$ and $R_3$, when taken together with the adjacent carbon atoms, may form a benzene ring.

14. A composition for occult blood detection according to claim 13, wherein
$R_1$ for compound I is
a $C_1 \sim C_3$ alkyl, a substituted or unsubstituted aralkenyl of the formula:

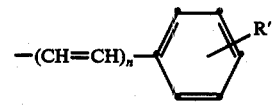

wherein $n$ is an integer of 1 to 2 and R' is a member selected from the group consisting of a hydrogen, a halogen, a $C_1 \sim C_3$ alkyl and a $C_1 \sim C_3$ alkoxy, or a substituted or unsubstituted aralkyl of the formula:

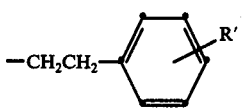

wherein R' has the same meaning as defined above;

R$_2$ and R$_3$ for compound I are each a hydrogen or a C$_1$~C$_3$ alkyl; and

R$_2$ and R$_3$, when taken together with the adjacent carbon atoms, may form a benzene ring.

15. A composition for occult blood detection in excreta or body fluids according to claim 13, wherein the thiazole compound is a member selected from the group consisting of 2-styryl-4-methylthiazole, 2-(p-methoxystyryl)-thiazole, 2-(p-ethoxystyryl)-thiazole, 2-(p-methoxystyryl)-4-methylthiazole, 2-styrylthiazole, 1-phenyl-4-thiazolyl-(2)-butadiene, 2-(p-methylstyryl)-thiazole, 2-(p-methoxystyryl)-benzothiazole, 2-(styryl)-benzothiazole, 2-(p-chlorostyryl)-thiazole, 2-(p-bromostyryl)-thiazole, 2-(p-fluorostyryl)-thiazole, 2,4-dimethylthiazole and 1-phenyl-2-(2-thiazole)ethane.

16. A composition for occult blood detection in excreta according to claim 13, wherein the hydroperoxide is a member selected from the group consisting of cumene hydroperoxide, p-menthane hydroperoxide, tetraline hydroperoxide, tert-butyl hydroperoxide, 2,5-dimethylhexane-2,5-dihydroperoxide and diisopropylbenzene hydroperoxide.

17. A method for detecting occult blood in excreta or body fluids, which comprises contacting the excreta or body fluids with a test strip or a composition comprising a chromogen, a hydroperoxide and, as a sensitizer, a thiazole compound (I) of the formula:

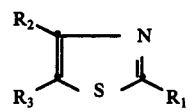

wherein R$_1$ is an alkyl, a substituted or unsubstituted aralkenyl, or a substituted or unsubstituted aralkyl; R$_2$ and R$_3$ are each a hydrogen or a lower alkyl; and R$_2$ and R$_3$, when taken together with the adjacent carbon atoms, may form a benzene ring.

18. A method for detecting occult blood in excreta or body fluids according to claim 17, wherein R$_1$ for compound I is a C$_1$~C$_3$ alkyl, a substituted or unsubstituted aralkenyl of the formula:

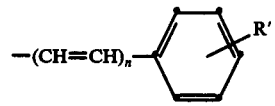

wherein n is an integer of 1 or 2 and R' is a member selected from the group consisting of a hydrogen, a halogen, a C$_1$~C$_3$ alkyl, and a C$_1$~C$_3$ alkoxy or a substituted or unsubstituted aralkyl of the formula:

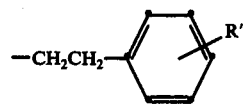

wherein R' has the same meaning as defined above; R$_2$ and R$_3$ for compound I are each a hydrogen atom or a C$_1$~C$_3$ alkyl; and R$_2$ and R$_3$, when taken together with the adjacent carbon atoms, may form a benzene ring.

* * * * *